US011497542B2

(12) United States Patent
Loeser

(10) Patent No.: US 11,497,542 B2
(45) Date of Patent: Nov. 15, 2022

(54) TISSUE FORCEPS

(71) Applicant: Erbe Elektromedizin GmbH, Tuebingen (DE)

(72) Inventor: David Loeser, Rottenburg am Neckar (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 574 days.

(21) Appl. No.: 16/592,096

(22) Filed: Oct. 3, 2019

(65) Prior Publication Data

US 2020/0107873 A1 Apr. 9, 2020

(30) Foreign Application Priority Data

Oct. 5, 2018 (EP) ..................................... 18198761

(51) Int. Cl.
*A61B 17/29* (2006.01)
*A61B 18/08* (2006.01)
(Continued)

(52) U.S. Cl.
CPC ............ *A61B 18/085* (2013.01); *A61B 17/29* (2013.01); *A61B 1/3132* (2013.01);
(Continued)

(58) Field of Classification Search
CPC ........................... A61B 18/085; A61B 1717/29
See application file for complete search history.

(56) References Cited

U.S. PATENT DOCUMENTS 4,815,476 A 3/1989 Clossick
5,190,541 A 3/1993 Abele et al.
(Continued)

FOREIGN PATENT DOCUMENTS

CA 2106039 A1 3/1994
CN 101779979 B 1/2013
(Continued)

OTHER PUBLICATIONS

European Search Report dated Mar. 14, 2019, in corresponding European Application No. 18198761.1 (7 pages).
(Continued)

*Primary Examiner* — Nathaniel C Chukwurah
(74) *Attorney, Agent, or Firm* — Fitch, Even, Tabin & Flannery LLP

(57) ABSTRACT

A forceps instrument comprises, for the support of at least one pivotally supported branch, a bearing insert which is inserted into a base in order to support at least one pivotable branch. The bearing insert may be inserted transversely with respect to the pivot axis into a corresponding compartment of the base and fixed there in the compartment, due to detent action. The bearing insert comprises two bearing elements, including cylindrical journals, which are arranged on bearing parts of the bearing insert, without being in contact with each other, the bearing parts having the form of plates, that are oriented parallel to each other. The two journals come into engagement with corresponding openings of the branch, in which case the distance remaining between the end sides of the journals can be used for the arrangement of miscellaneous elements, including a cutting knife.

15 Claims, 9 Drawing Sheets

(51) Int. Cl.
  *A61B 1/313* (2006.01)
  *A61B 18/14* (2006.01)
  *A61B 18/00* (2006.01)

(52) U.S. Cl.
  CPC ... *A61B 18/1445* (2013.01); *A61B 2017/2902* (2013.01); *A61B 2018/00595* (2013.01); *A61B 2018/00601* (2013.01)

(56) References Cited

U.S. PATENT DOCUMENTS

| | | |
|---|---|---|
| 6,113,598 A | 9/2000 | Baker |
| 6,585,735 B1 | 7/2003 | Frazier et al. |
| 6,656,177 B2 | 12/2003 | Truckai et al. |
| 8,394,094 B2 | 3/2013 | Edwards et al. |
| 9,757,138 B2 | 9/2017 | Guba et al. |
| 2002/0115997 A1 | 8/2002 | Truckai et al. |
| 2002/0143358 A1 | 10/2002 | Domingo et al. |
| 2003/0216733 A1 | 11/2003 | McClurken et al. |
| 2004/0044363 A1 | 3/2004 | Fowler |
| 2005/0113826 A1 | 5/2005 | Johnson et al. |
| 2005/0159745 A1 | 7/2005 | Truckai et al. |
| 2005/0222602 A1* | 10/2005 | Sutter ............... A61B 18/1445 606/192 |
| 2009/0326531 A1 | 12/2009 | Geiselhart |
| 2011/0082494 A1 | 4/2011 | Kerr et al. |
| 2011/0257680 A1 | 10/2011 | Reschke et al. |
| 2013/0085516 A1 | 4/2013 | Kerr et al. |
| 2015/0073451 A1 | 3/2015 | Guba et al. |
| 2015/0374430 A1 | 12/2015 | Weiler et al. |

FOREIGN PATENT DOCUMENTS

| | | |
|---|---|---|
| DE | 102004013530 A1 | 10/2005 |
| DE | 202007009165 U1 | 8/2007 |
| DE | 102006062848 B4 | 1/2013 |
| EP | 0745355 A1 | 12/1996 |
| EP | 1958583 A2 | 8/2008 |
| EP | 2959854 A1 | 12/2015 |
| EP | 2845548 B1 | 11/2016 |
| GB | 2470314 B | 6/2012 |
| RU | 2012108960 A | 9/2013 |
| WO | 00/47124 A1 | 8/2000 |
| WO | 2008040483 A1 | 4/2008 |

OTHER PUBLICATIONS

Russian Office Action and Search Report for Application No. 2019130405/14(059747) dated Aug. 16, 2022, 12 pages.
Government of India, Office Action and Search Report for Application No. 201914040060 dated Aug. 30, 2022, 5 pages.

* cited by examiner

TISSUE FORCEPS

RELATED APPLICATION(S)

This application claims the benefit of European Patent Application No. 18198761.1, filed Oct. 5, 2018, the contents of which are incorporated herein by reference as if fully rewritten herein.

TECHNICAL FIELD

The invention relates to a tissue forceps or a like instrument, in particular in the embodiment as a laparoscopic instrument.

BACKGROUND

Publication EP 2 959 854 A1 discloses a tissue forceps configured as a laparoscopic instrument, said forceps having, on the distal end of an elongated shaft, a tool with two branches between which tissue is to be grasped, coagulated and optionally severed. While one of the branches is rigidly connected to the shaft, the other branch is supported so as to be pivotable relative to the latter. A cross pin acts as a support for the branch, said cross pin extending through a base receiving the proximal end of the movable branch, as well as through the proximal end of the movable branch.

In tissue forceps or tissue scissors, the configuration of a swivel joint for the pivotable support of one or two branches is frequently accomplished in by means of a cross pin. Typical examples relating thereto can be learned from publications US 2005/0113826 A1, EP 1 958 583 A2, WO 00/47124, US 2011/0257680 A1, US 2005/0159745 A1, US 2002/0115997 A1, GB 2 470 314 B, U.S. Pat. No. 8,394,094 B2, U.S. Pat. No. 6,113,598, US 2011/0082494 A1, US 2013/0085516 A1, DE 10 2006 062 848 B4, U.S. Pat. No. 6,585,735 B1, US 2002/0143358 A1, US 2003/0216733 A1, WO 2008/040483 A1, as well as from US 2004/0044363 A1.

Furthermore, it has been known to support two branches of a forceps-like instrument at spaced apart points, respectively, by means of a cross pin. Publication CN 101779979 B, as well as EP 2 845 548 B1, are referred to as examples. In doing so, the two movably supported branches are individually pivotally supported on a base, in which case there is a space between the two bearing points through which a knife can be inserted in a slit defined by the two branches in closed state.

If a cross pin is used for supporting one or both branches, this cross pin is in the way of other elements to be used in the region of the branches. Such an element may be a knife, for example, that is to be supported in the region of the forceps instrument so as to be axially movable in the distal direction of the forceps instrument. However, if the branch support is moved out of the center of the cross-section so that the path is clear for a knife or other element, this contributes to an enlargement of the overall cross-section of the instrument, thus preventing a slimming of the instrument.

Publication U.S. Pat. No. 6,656,177 B2 describes a cauterizing forceps with one pivotable branch which is supported by two journals that are in alignment with each other. They are seated in a proximal end of the fixed branch, respectively laterally. The respective diameters of the two journals is small, which is why the journals should be made of an appropriately shear-resistant material.

It is the object of the invention to state a concept for a tissue forceps that allows a slim and, at the same time, robust construction. Furthermore, a simple manufacture should be possible.

SUMMARY

This object is achieved with the tissue forceps as described herein.

The forceps instrument according to the invention has two branches, at least one of them being held so as to be pivotally movable, so that the branches are able to grasp and compress tissue between them. A base having a support structure comprising two bearing elements arranged coaxially with respect to each other and, together forming a bearing pin are adapted for supporting the branches. The end sides of the two bearing elements may touch each other or—as is preferred—define a distance between each other.

The movable branch thus extends through both bearing elements such that these bearing elements can extend into two openings that are provided on the second branch at two sides facing away from each other. The two openings are arranged coaxially with respect to each other and preferably have a circular cross-section. Likewise, the two bearing elements can be arranged coaxially with respect to each other and preferably have a circular cross-section. Further preferably, the two bearing elements are configured as journals, preferably as cylindrical journals.

This bearing arrangement forms a joint that can be arranged approximately centered relative to its cross-section. Despite this centered arrangement, there is the option of providing elements passing through the center of the base such as, a cutting knife or the like, for example. Independently thereof, a space-saving robust bearing structure is created that requires only a few components that are inexpensive to manufacture and easy to assemble.

The arrangement is particularly easy to assemble when the bearing structure is provided on a bearing insert that can be connected to the base. In particular suitable for a connection to the base is a positive-locking connection, in that the bearing insert is preferably inserted into the base transversely with respect to the pivot axis and is snapped into said base. To do so, the base and the bearing insert may have appropriate detent structures. Alternatively and/or additionally, a connecting structure may be provided for the stationary support of the bearing insert in the base. The connecting structure preferably comprises elements that come into engagement with each other in a guided manner, wherein the guiding direction of said elements is oriented transversely with respect to the pivot axis. For example, the bearing insert may have projections, for example prismatic projections, that are associated with matching grooves provided on the base. Preferably, these grooves are arranged in the facing arranged walls of a receiving compartment provided in the base, said compartment extending through the base. Consequently, said compartment has both a first window, through which can extend the second branch, and a second window for the insertion of the bearing insert into the receiving compartment.

The bearing insert may be formed of two mirror-symmetrically molded parts, in particular, injection-molded parts, in particular of plastic material, said molded parts holding between them the second branch. Furthermore, the two molded parts may be connected to each other by a strip, a wall, a journal or the like, and thus form a one-piece injection-molded part. This results in a simple manufacture and a simple assembly. Each of the two molded parts may comprise a plate which, in mounted state, abuts against one side of the branch and from which extends a bearing element into an opening of the branch. The bearing insert can thus perform a double function: it is part of the pivot bearing of the branch and it effects a safe electrical insulation of the branch relative to the base, which base may be connected to the other branch in an electrically conductive manner. In this way, electrical voltages of several 100 Volts can be safely maintained.

The plastic material that is suitable, in particular, is PEEK or LCP. PPA (polyphthalamide), PPS (polyphenylene sulfide) or PAI (polyamide imide) may also be used.

In the forceps instrument according to the invention, the bearing axle consisting of two journals is manufactured completely of plastic material. Because there remains a passage between the journals, there is room for passing through knives or supply lines. The journals may have a very large diameter, thus allowing the absorption of large bearing forces and thus the generation of great contact forces between the branches of the instrument. For example, the journals may have a diameter that is at least as large as the height of the pivotable branch to be measured in pivoting direction. As a result of this, a large journal cross-sectional surface and thus a high maximum bearing response force are achieved, without overstraining the plastic journal in view of its shearing strength.

The guiding structure selected on the bearing insert may comprise projections that are configured on two sides of the bearing insert that face away from each other. Preferably, these projections have an acute-angled corner which points in the direction of force when the forceps instrument is closed. In addition, the upper side of each projection may be slightly rounded. In this way, a secure hold of the bearing insert in the base can be aided. The rounding of the surface can be used to take pressure off the detent arrangement which holds the bearing insert in the base when the branch is being closed in order to ensure that the bearing insert is securely seated. This geometric configuration can be utilized to cause a self-clamping due to the bearing response force when the mouth part is closed, in that the bearing insert is pressed into its seat.

The invention also relates to a method for providing a forceps instrument, wherein the bearing structure is initially provided, e.g., as an injection-molded part in the form of an elongated, flat part. In this case, both bearing parts and a connecting strip are initially arranged in a common plane or at an oblique angle with respect to each other.

Thereafter, the bearing parts are moved into two parallel, spaced apart planes, namely by bending or removing or interrupting the connecting strip. At least one part to be supported may be arranged between the bearing parts and inserted therewith into the compartment of the base.

BRIEF DESCRIPTION OF THE DRAWINGS

Additional details of advantageous embodiments of the invention are the subject matter of the description or the claims and the drawings. They show in FIG. 1 a schematic perspective overview display of a forceps instrument according to the invention, FIG. 2 a perspective schematic diagram of the distal end of the forceps instrument according to the invention, FIG. 3 a perspective representation of individual parts of the forceps instruments according to FIG. 2, FIG. 4 a perspective view of the underside of the forceps instrument according to FIG. 2, FIG. 5 a perspective exploded view of a modified embodiment of the forceps instrument according to the invention, FIG. 6 a sketched representation of the forces acting on the forceps instrument, FIG. 7 a cross-sectional representation of the forceps instrument, cut away in the region of its bearing arrangement, and simplified, FIG. 8 a perspective exploded view of a further modified embodiment of the forceps instrument according to the invention, FIG. 9 a perspective representation of a bearing insert for a forceps instrument according to the invention, in assembled position, FIG. 10 a perspective representation with a view onto the outside of a bearing insert for a forceps instrument according to the invention, following manufacture, FIG. 11 a perspective representation with a view into the inside of the bearing insert according to FIG. 10.

DETAILED DESCRIPTION

Figure 1:
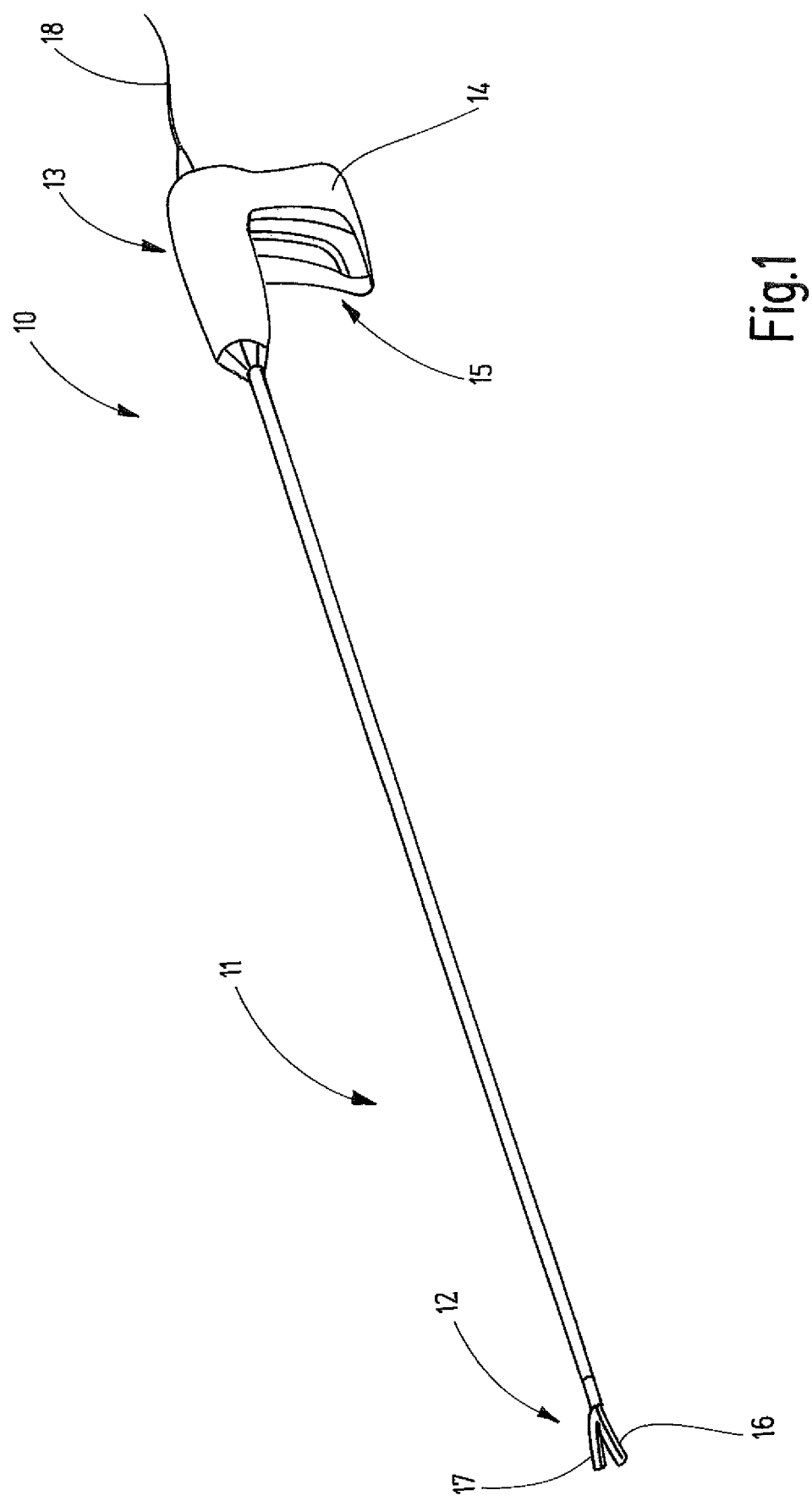

FIG. 1 shows a forceps instrument 10 that is depicted here as an example of a laparoscopic instrument having a shaft 11 that supports a cauterizing forceps 12 on its end. On its proximal end, the shaft 11 is supported by a housing 13 that has a handle 14 and an actuating element 15. The latter is adapted for actuating the cauterizing forceps 12. The cauterizing forceps 12 has two branches, namely a first branch 16 and a second branch 17, in which case at least one of these is movably supported, and, in the present exemplary embodiment, can be subjected to HF current in order to coagulate tissue grasped between them. To do so, the forceps instrument 10 is connected—via a cable 18—to a not specifically illustrated generator.

It is pointed out that, instead of the forceps instrument 10 within the framework of the invention, it is possible to also consider other instruments that comprise two branches 16 and 17, at least one of which being supported so as to be movable relative to the other. The spectrum of use encompasses instruments for open surgical applications, with or without shaft, laparoscopic instruments, as well as instruments for endoscopic use. The spectrum of use encompasses instruments with electrically activated branches 16, 17 as well as instruments with branches that only have a mechanical function for clamping and cutting and cannot be activated by the application of an electrical current. Furthermore, the spectrum of use encompasses instruments with a cutting device, for example a knife, that is to be moved in or on the branches 16, 17, as well as instruments without a knife. The spectrum of use of the invention also encompasses forceps instruments with stationary knives, for example electrically charged cutting electrodes.

Figure 2:
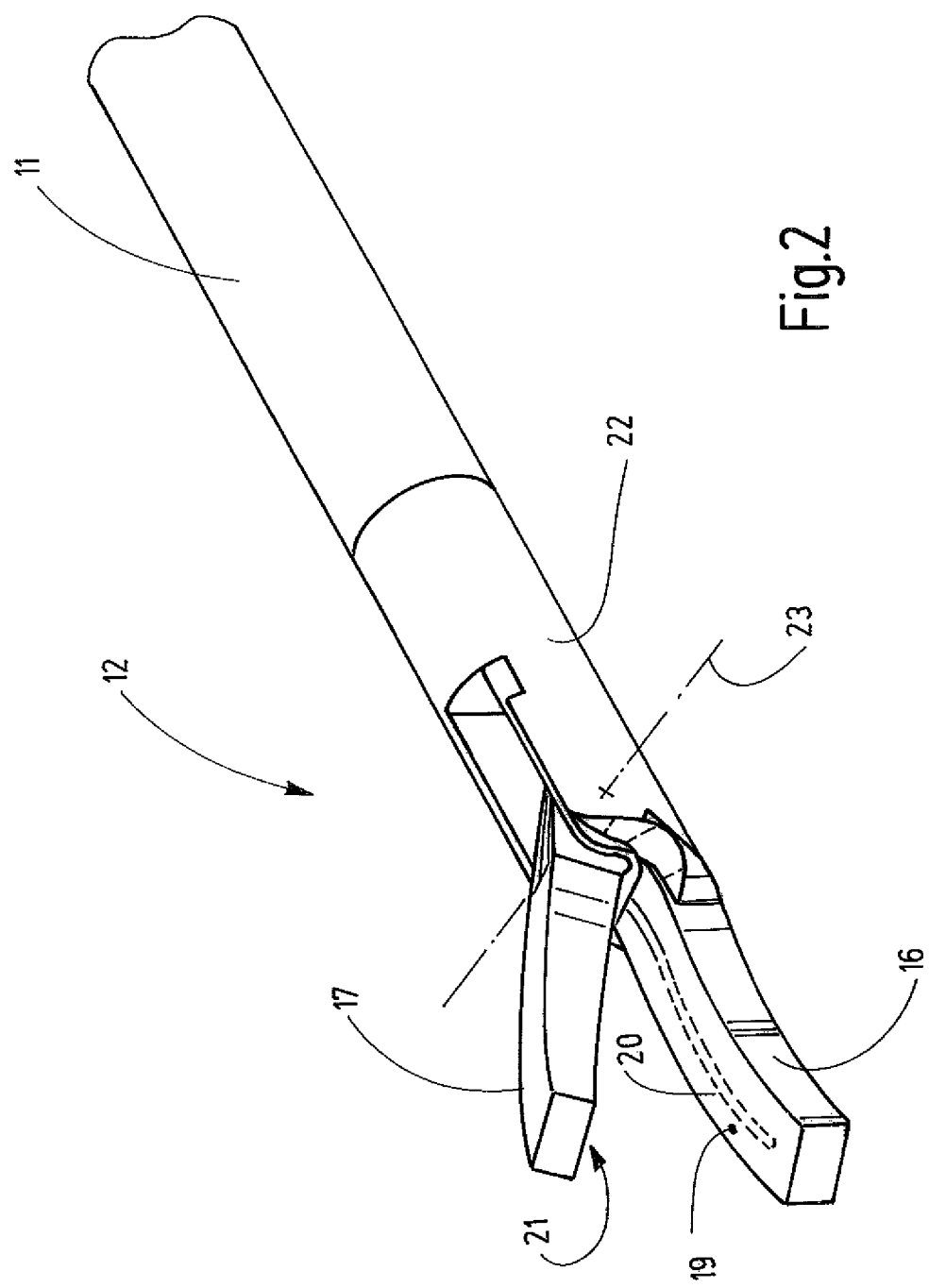

FIG. 2 is an enlarged view of the cauterizing forceps 12. The first branch 16 has a tissue contact surface 19 facing the second branch 17, said contact surface 19 being flat, for example. Preferably, the tissue contact surface 19 is electrically conductive in order to be supplied with an electrical voltage and current via the cable 18. The branch 16 may be straight or, as shown, be slightly laterally curved. Optionally, it is possible, for example, to form an elongated slit 20 in the tissue contact surface 19, as shown, for example, in dashed lines in FIG. 2. This elongated slit may be adapted for guiding a not specifically illustrated, axially movable cutting nice. Likewise, the second branch 17 is provided with a tissue contact surface on its side facing the first branch 16, said surface being preferably flat. The two branches 16, 17 preferably have the same contour, so that they will meet matching the two tissue contact surfaces 19, 21 on top of each other when the second branch 17 is folded onto the first branch 16. Also, the second branch 17 may be provided with a slit to guide a knife. Preferably, the tissue contact surface 21 is configured so as to be electrically conductive and, for example, be connectable to the generator via the cable 18.

As can further be inferred from FIG. 2, the two branches 16, 17 are held on a base 22 that is arranged on the distal end of the shaft 11. In doing so, the first branch 16 is preferably immovably connected to the base 22. For example, said first branch may be an extension of the base 22, so that the first branch 16 and the base 22 form a one-piece part consisting, for example, of plastic material or ceramic or also of metal.

The second branch 17 is supported by the base 22 so as to be pivotable about a pivot axis 23 that is oriented transversely with respect to the longitudinal direction of the shaft 11. Preferably, the pivot axis is located approximately on the center, i.e., on the diameter of the base cross-section.

Figure 3:
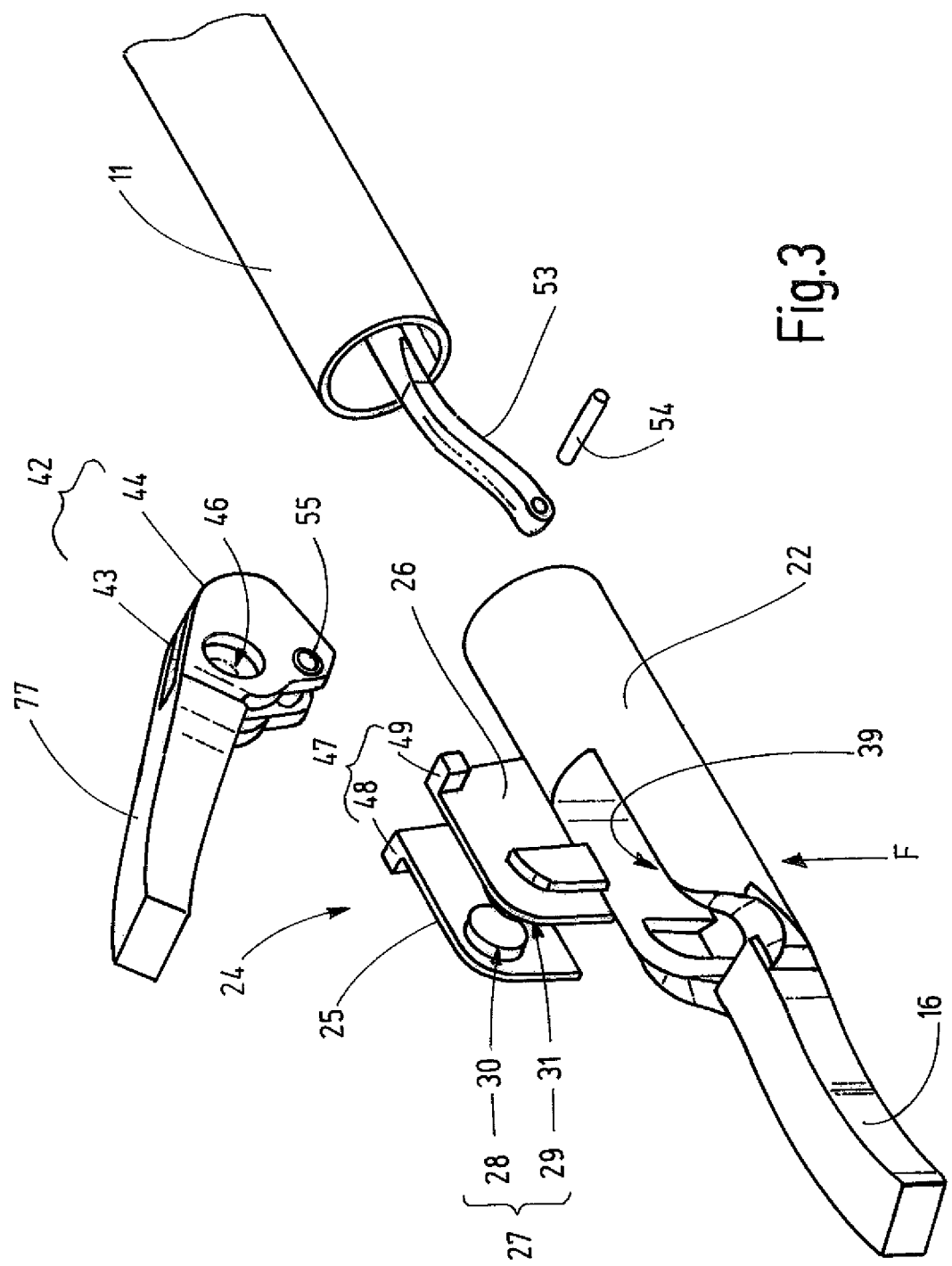

As can be inferred, in particular from FIG. 3, a bearing insert 24 that may be configured as one piece or as two pieces is adapted for the pivotable support of the second branch 17, and comprises, for example, two mirror-symmetrical (or also differently configured) bearing parts 25, 26. They can be provided as separate parts or be connected to each other by a strip which is concealed in FIG. 3 and arranged, for example on the right lower end. In doing so, the connection is configured in such a manner that the two bearing parts 25, 26 can minimally bounce toward each other or away from each other.

Preferably, the bearing insert 24 is an injection-molded part which is associated with two bearing parts 25, 26 and which is formed and provided separately from the branches 16, 17. However, it is also possible to directly attach the bearing insert to one of the branches 16, 17 by injection-molding. Each of the two bearing parts 25, 26 preferably consists of a plate-shaped base section on which additional structures are formed; in particular, a bearing structure 27 is formed in this manner, said structure being associated with two bearing elements 28, 29. Preferably, the bearing element 28 is a cylindrical journal 30 that extends from one flat side of the bearing part 25 to the other bearing part 26. Likewise, the bearing element 29 is preferably formed by a journal 31 that extends from the bearing element 26 to the bearing element 25. Preferably, the two journals 30, 31 are cylindrical journals which include between them a distance A that is also particularly obvious from FIG. 7. However, it is also possible to configure the length of the journals 30, 31 in such a manner that they contact each other their end sides or on projections provided on the end sides. The diameters of the journals preferably range between 1 mm and 3 mm. Because of this relatively large diameter the bearing insert 24 can be made of plastic. At the same time, a particularly slim design of the forceps tool is made possible, in which case the hinge region has a relatively small diameter of, e.g., only 5 mm-5.7 mm.

Figure 7:
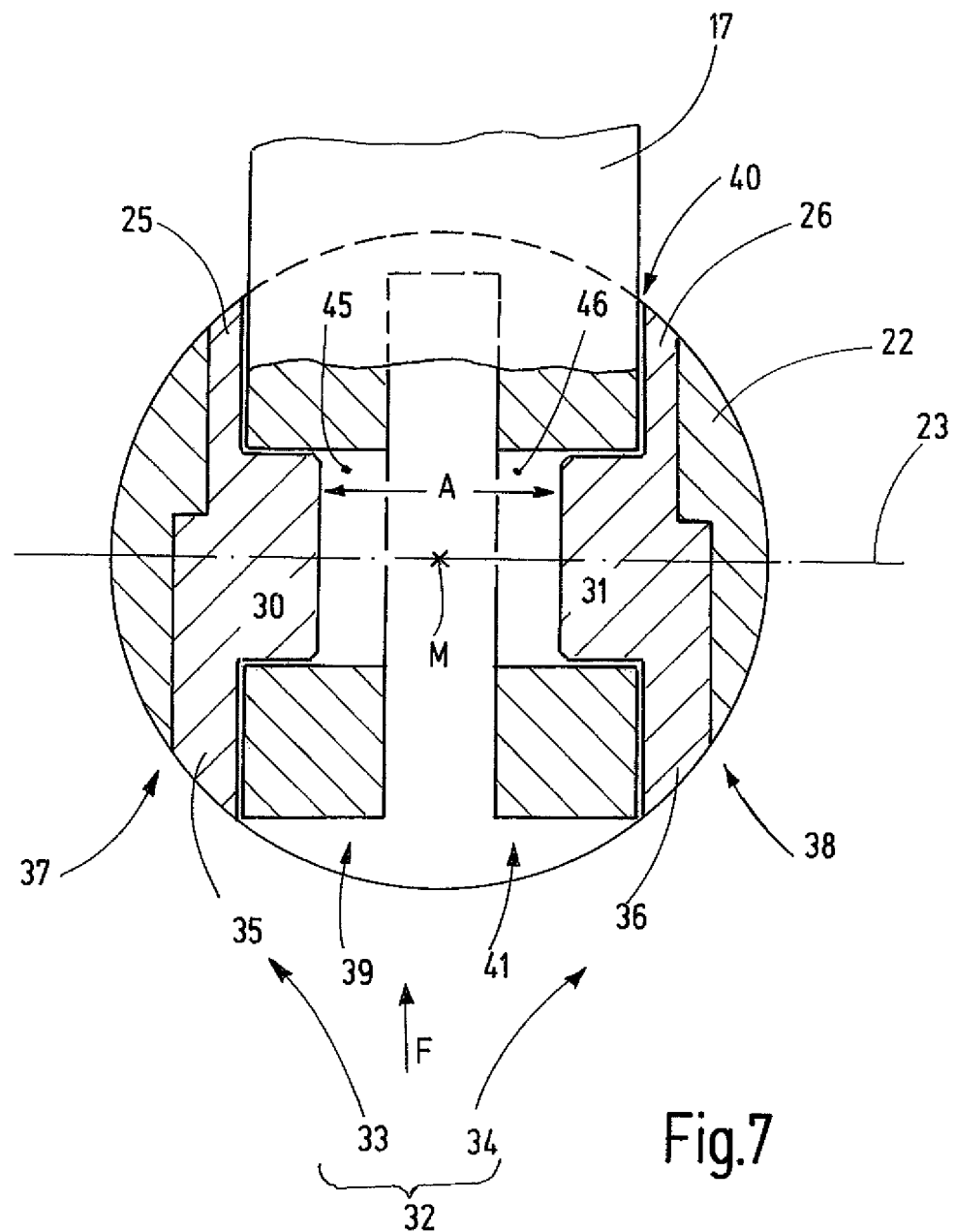

The bearing parts 25, 26 are provided—on their sides facing away from one another—with guide elements 33, 34 that belong to a connecting structure 32. Preferably, these projections 35, 36 are preferably prismatic projections that are delimited on their parallel flanks and are rectangular or trapezoidal in plan view, said projections fitting in a direction transverse to the pivot axis 23 into corresponding grooves 37, 38 on the base 22. The grooves 37, 38 are formed on walls of a compartment 39 facing one another (FIG. 3 in conjunction with FIG. 7), into which compartment the bearing insert 24 can be inserted transversely with respect to the pivot axis 23. To do so, the compartment 39 has an upper window 40 from which extends the second branch 17, and a lower window, through which the bearing insert 24 can be inserted into the compartment 39. Consequently, in plan view, the compartment 29 forms an approximately rectangular passage opening through the base 22. The parallel flanks of the two projections 35, 36 are oriented transversely with respect to the pivot axis 23 and thus define—in conjunction with the grooves 37, 3—a guiding direction F that is transverse to the pivot axis 23 and, at the same time, extends transversely with respect to the longitudinal axis of the shaft 11. In FIGS. 3 and 7, this guiding direction F is only marked by an arrow for clarification. Other guiding directions are possible The second branch 17 has, on its proximal end, a hinge section 42 that may comprise two wall sections 43, 44 parallel to each other; in which case each of the two parallel wall sections 43, 44 is provided with an opening 45, 46, wherein the openings 45, 46 may preferably be arranged coaxially with respect to each other. In doing so, the diameter of the two openings 45, 46 may be minimally larger than the diameter of the two preferably cylindrical journals 30, 31. In doing so, the arrangement of the pins 30, 31 and the openings 45, 46 is preferably such that the center M of the cross-section of the base 21 is located within a cylinder defined by the openings 45, 46. In the example according to FIG. 7 the center M is located approximately on the pivot axis 23, which, however, is not absolutely necessary. Also, in the event of an offset of the center M relative to the pivot axis 23 within the aforementioned condition (center M is located within the cylinder defined by the openings 45, 46), it is possible to achieve a slim and robust, easy to assemble design for the pivot bearing of the branch 17.

Figure 5:
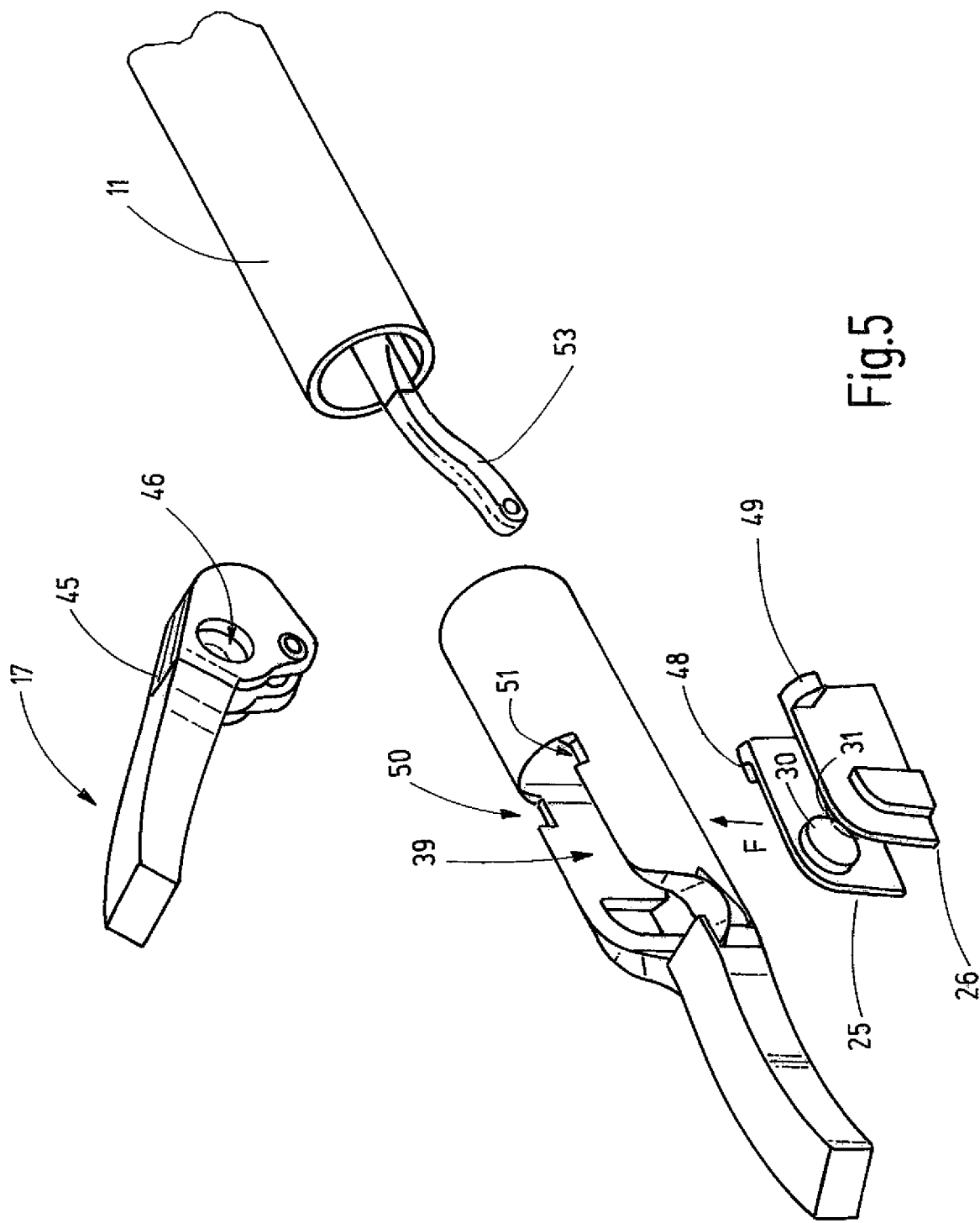
Figure 6:
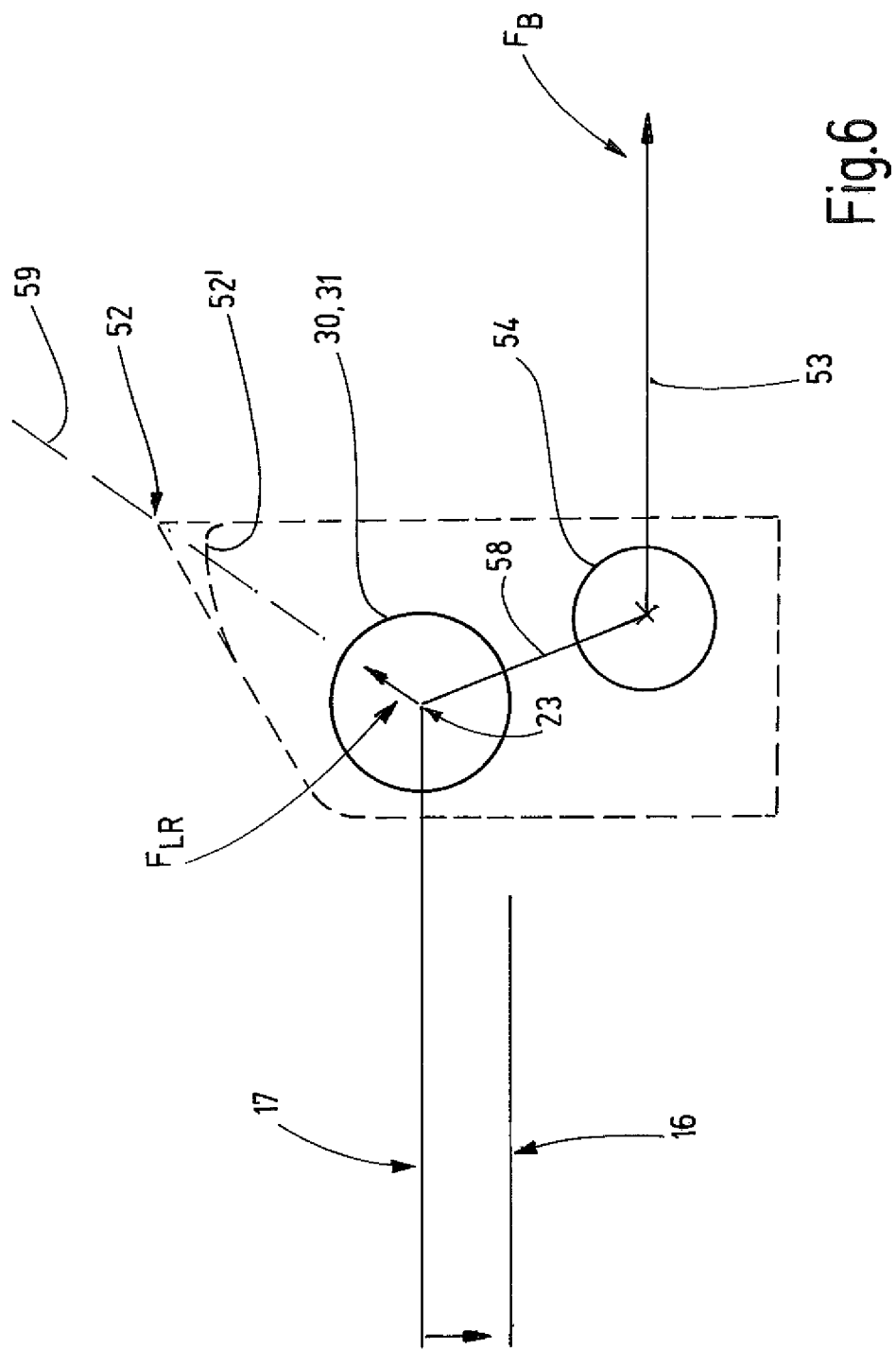

The connecting structure 32 may be configured as a detent arrangement, in that additional projections, for example detent projections are formed on the projection 35, 36, said additional projections engaging in the recesses of the grooves 37, 38. Alternatively, detent projections 48, 49 may be provided as the detent arrangement 47 at other locations of the bearing parts 25, 26, as is illustrated, in principle, by FIG. 3. Alternatively, as illustrated by FIG. 5, the detent projections 48, 49 may be associated with corresponding detent recesses 50, 51 such as are formed, for example on the upper edge of the compartment 39. For assembly, the branch 17 is initially arranged between the bearing parts 25, 26 in such a manner that their journals 30, 31 engage in the openings 45, 46. Thereafter, the bearing parts 25, 26 are resiliently compressed, and this arrangement is inserted from the bottom in the direction F into the compartment 39 until the detent projections 48, 49 snap into the recesses 50, 51. In doing so, the projections 35, 36 move in the grooves 37, 38 in guiding direction F until their respective upper corners strike corresponding, preferably acute-angled corners of the associate grooves 37, 38. Regarding this, FIG. 6 shows such an upper corner 52 on the dashed-line contour of a groove 37, 38. In doing so, the dashed line 52' illustrates the at least preferably rounded upper side or surface of the projection 35 and/or 36.

The branch 17 is associated with an actuating rod 53 as can be seen in FIGS. 3 and 5. For example, this actuating rod is connected via a cross pin 54 to the branch 17 that has an appropriate coupling opening 55 for this purpose.

Figure 4:
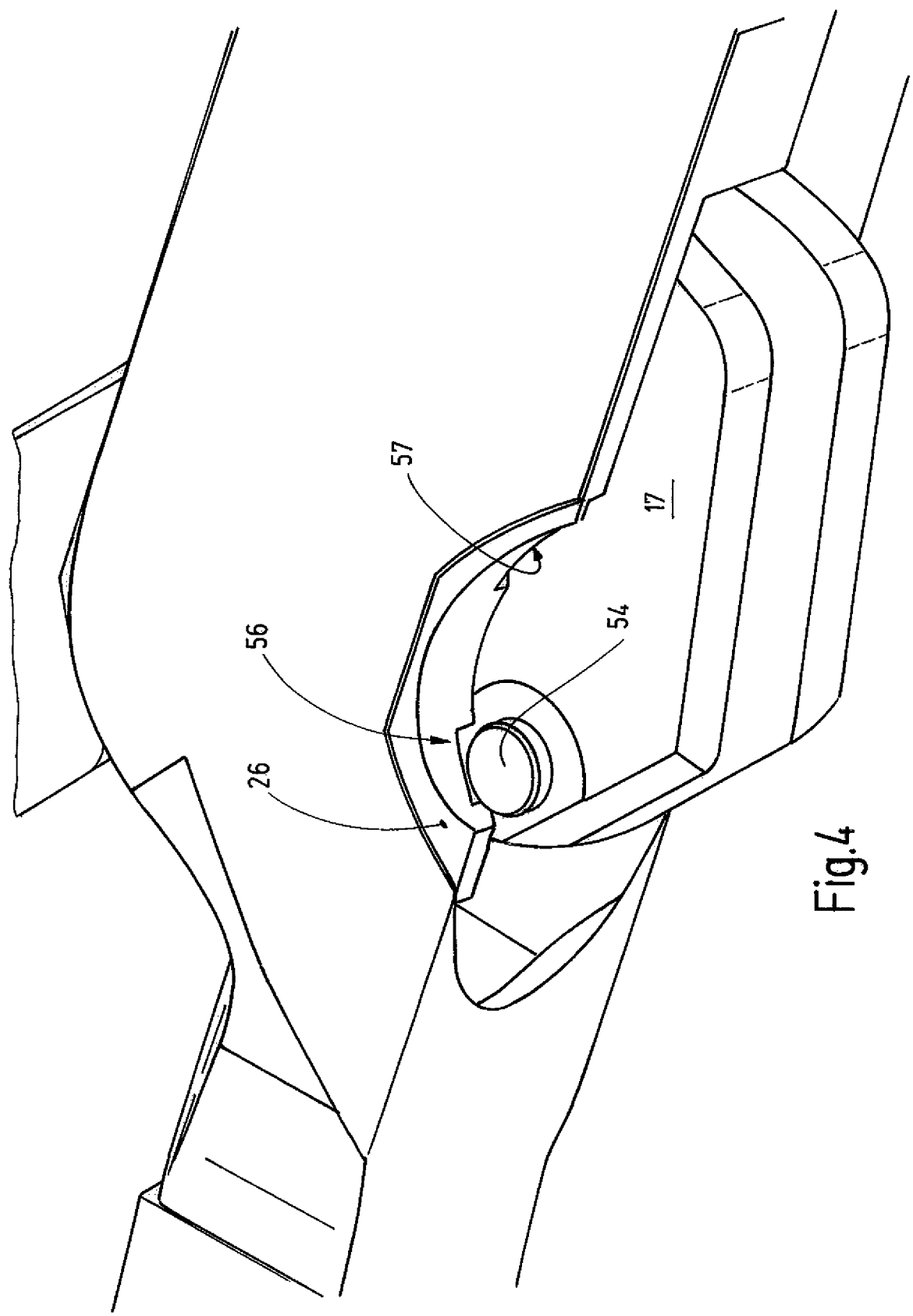

As can be seen in FIG. 4, each of the two ends of the pin 54 may slightly project beyond the outside surface of the branch 17, as shown by FIG. 4 on the end of the pin 54 facing the viewer. The bearing part 26 (as well as the bearing part 25 that is concealed in FIG. 4) may have—for the end of the pin 54 in both end positions of the branch 17 (i.e., in fully open, as well as in fully closed state)—a pocket 56, 57 each, which pocket receives the end of the pin 54 and secures said pin relative to its longitudinal direction (that is parallel to the pivot axis 23). Consequently, an inadvertent loss of the pin 54 during operation is not possible, while the assembly and disassembly thereof is easily possible in an intermediate position of the branch 17 between the fully closed position and the fully open position.

Regarding function and kinematics of the forceps instrument 10, reference is made to FIG. 6, which illustrates—in addition to the already addressed contour of the guide element 33 and 34 indicated in dashed lines—the common circular contour of the journals 33, 31, said journals being concentric to the pivot axis 23. Consequently, there results—relative to the center of the pin 54—a lever arm 58 that can be in pulling contact with the actuating rod 53 with an actuating force $F_B$. The branch 17 that is only schematically depicted in FIG. 6 is thus biased in the direction toward the branch 16. In doing so, bearing response forces $F_{LR}$ occur on the bearing device formed by the journals 30, 31, the direction of said forces being indicated in FIG. 6 by an arrow and a chain line 59 drawn in the direction of the arrow. This bearing response force $F_{LR}$ preferably points—at least approximately—in the direction of the corner 52, so that the chain line 59 extends through this corner. Consequently, it is overall possible to set the bearing insert 24 and relieve the detent device 47, so that—even with the application of great force to the branches 16, 17—it is ensured that the bearing insert 24 stays properly in its installed position.

Figure 8:
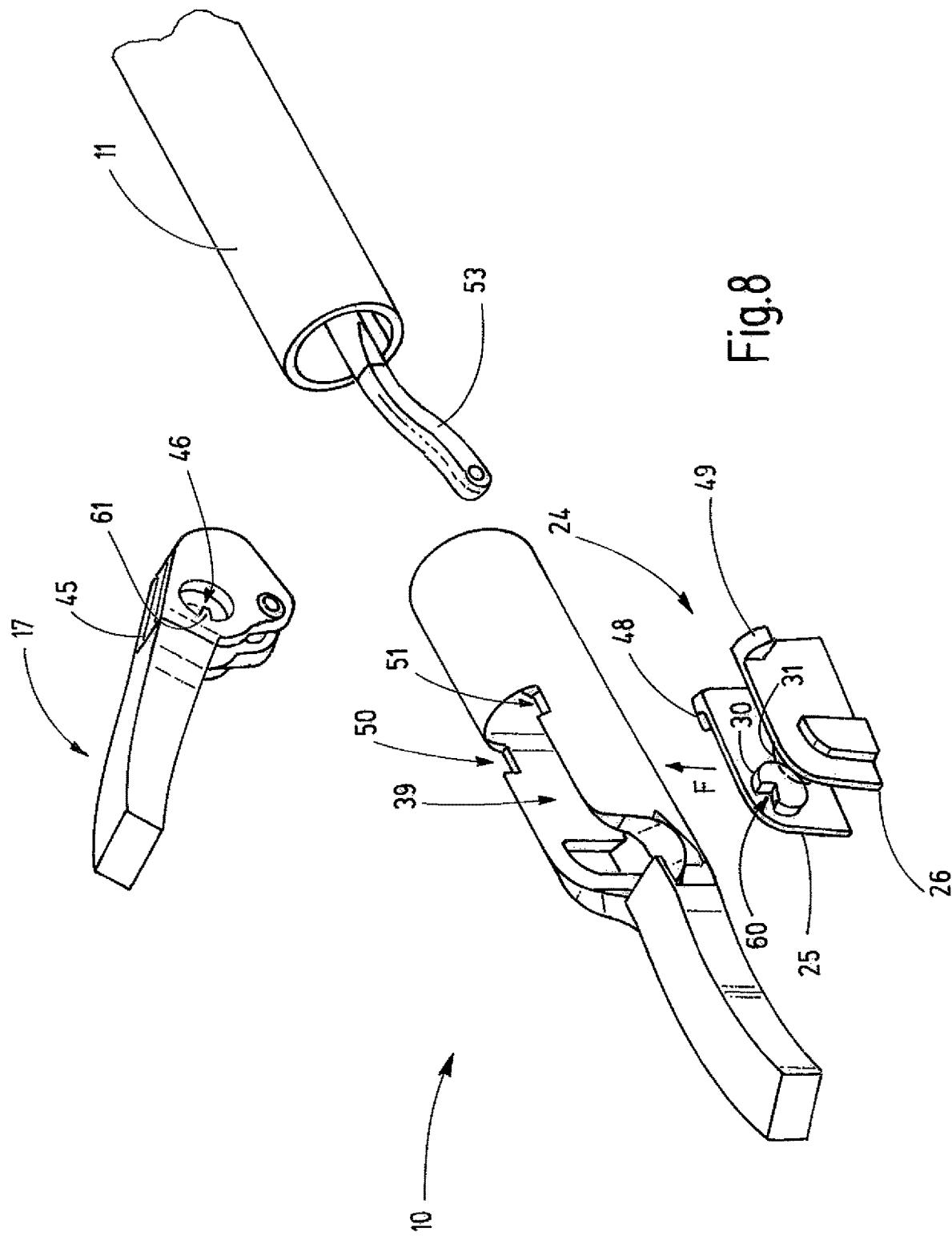

FIG. 8 shows a further embodiment of the forceps instrument 10, in which case, regarding its structure and function, initial reference is made to the description hereinabove, in particular the description of the embodiment according to FIG. 5. In the case of the forceps instrument 10 according to FIG. 8, there is effective—between the bearing insert 24 and the branch 17—a rotation angle limiting device 60 that, here, is exemplarily formed by a recess provided in at least one of the journals 30, 31. This recess is associated with a projection 61 provided on the edge of the opening 45, 46, said projection being movable in a limited manner in the recess in circumferential direction of the journal 30, 31. As a result of this, the maximum pivot angle of the branch 17 is limited.

Figure 9:
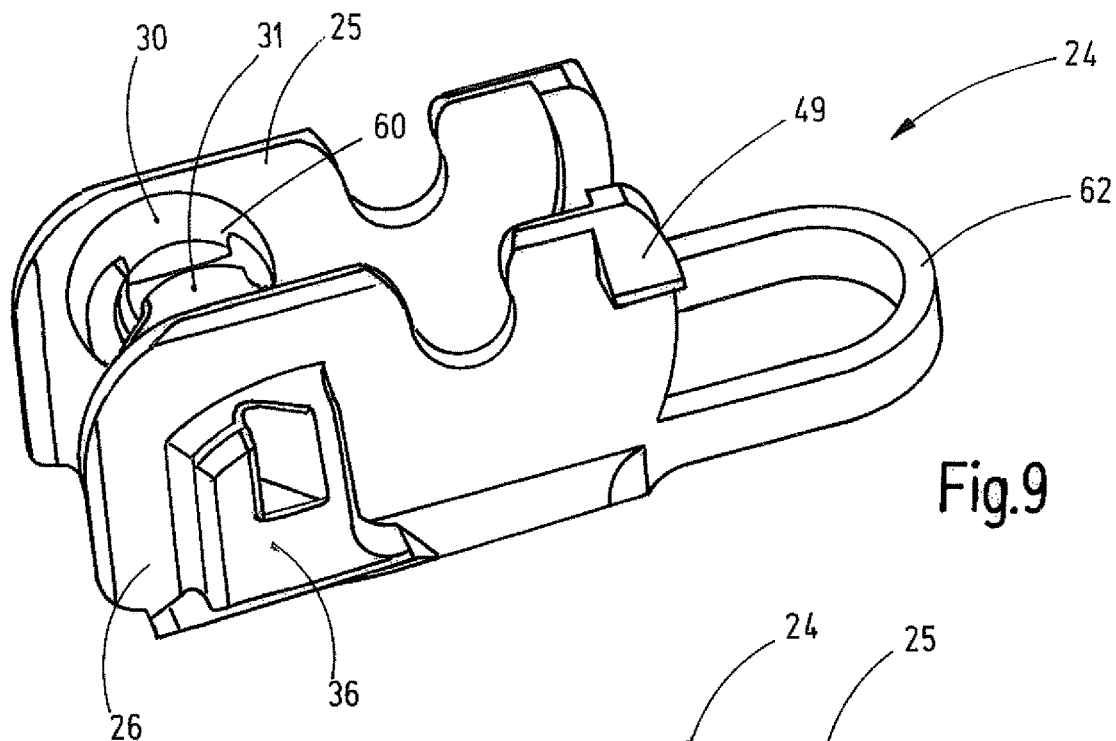

FIG. 9 shows a modified embodiment of a bearing insert 24 which, for example, may be made as an injection-molded part. Elements of this bearing insert 24 which have the same function and/or structure as the bearing inserts described hereinabove, will have the reference signs that have already been introduced in FIG. 9. The description of the embodiments according to FIGS. 1 to 8 applies analogously to the bearing insert 24 according to FIG. 9. The bearing insert 24 is shown in its installed position, in which the bearing parts 25, 26 are arranged next to each other in planes that are spaced apart. A strip 62 connecting the two bearing parts 25, 26 in one piece is bent in a u-shape under elastic and/or plastic deformation.

Figure 10:
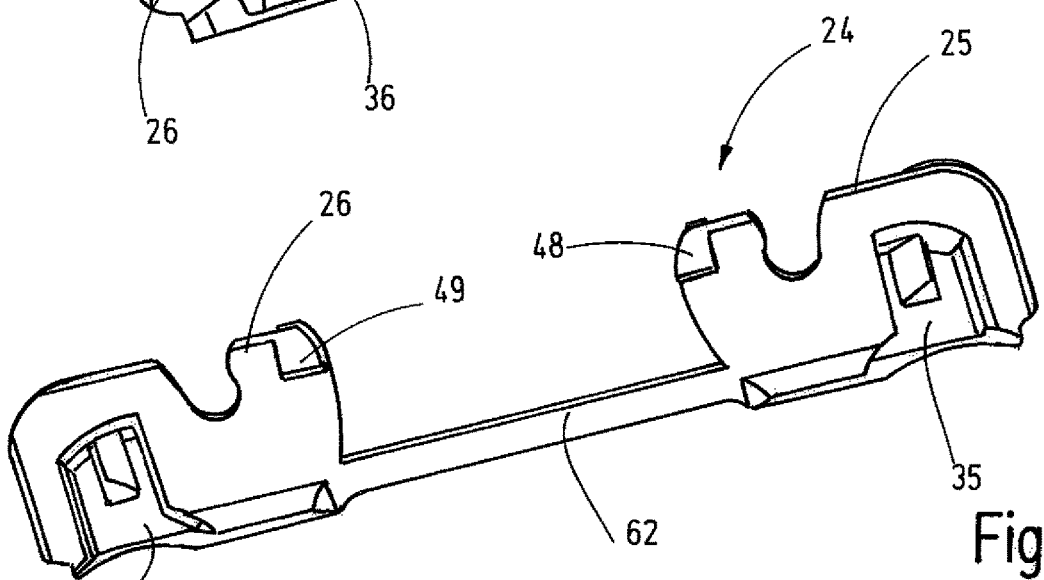
Figure 11:
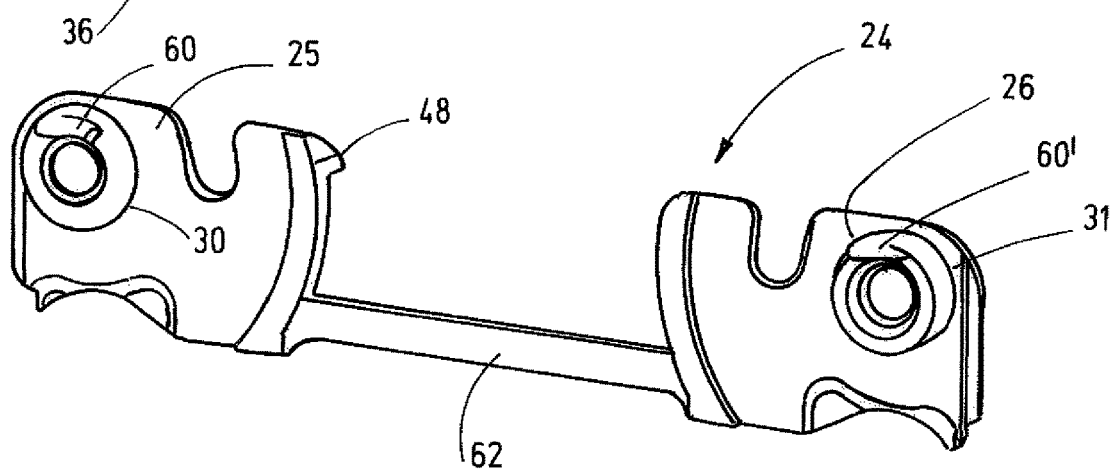

FIGS. 10 and 11 show the bearing insert 24 in stretched position following the manufacture, e.g., directly after the removal from an injection mold. The bearing insert can be easily handled and stored in this mold. Before installation in a forceps instrument, it is converted into the form according to FIG. 9. To act as the rotation angle limiting device 60, 60', the journal 30, 31 may have a lug on its end side. Furthermore, the journal 30, 31 may be hollow and/or exhibit additional structures.

The projections 35, 36 may be solid or have one or more recesses on their outside. These recesses may be configured as grooves, for example, in order to accomplish an interlocking with structures in the compartment 39.

The forceps instrument 10 according to the invention comprises, for the support of at least one pivotally supported branch 17, a bearing insert 24 which is inserted into a base 22 in order to support at least one pivotable branch 17. To do so, the bearing insert 24 is inserted—for example, transversely with respect to the pivot axis 23—into a corresponding compartment 39 of the base 22 and fixed there in the compartment 39, for example due to detent action. The bearing insert 24 comprises two bearing elements 28, 29, for example in the form of cylindrical journals 30, 31, which are arranged on bearing parts 25, 26 of the bearing insert 24, without being in contact with each other, said bearing parts having the form of plates, for example, that are oriented parallel to each other. The two journals 30, 31 come into engagement with corresponding openings 45, 46 of the branch 17, in which case the distance A remaining between the end sides of the journals 30, 31 can be used for the arrangement of miscellaneous elements such as, for example, a cutting knife.

REFERENCE SIGNS

10 Forceps instrument
11 Shaft
12 Cauterizing forceps
13 Housing
14 Handle
15 Actuating element
16 First branch
17 Second branch
18 Cable
19 Tissue contact surface
20 Elongated slit
21 Tissue contact surface
22 Base
23 Pivot axis
24 Bearing insert
25, 26 Bearing parts
27 Bearing structure
28, 29 Bearing elements
30, 31 Journals
A Distance of the end sides from the pins 30, 31
32 Connecting structure
33, 34 Guide elements
35, 36 Projections
37, 38 Grooves
39 Compartment for receiving the bearing insert
40 Upper window
41 Lower window
42 Hinge section
43, 44 Wall section
45, 46 Opening
M Center of cross-section of the cylindrical base 22
47 Detent device
48, 49 Detent projections
50, 51 Recesses
52 Corner
52' Upper side of the projection 35, 36
53 Actuating rod
54 Pin
55 Coupling opening
56, 57 Pockets for securing the pin 54
58 Lever arm
$F_B$ Actuating force
$F_{LR}$ Bearing response force 59 Chain line
60, 60' Rotation angle limiting device
61 Projection
62 Strip

The invention claimed is:

1. A forceps instrument (10) for the treatment of biological tissue, comprising:
   a first branch (16) that is held on a base (22) and extends away from said base,
   a second branch (17) that is held on the base (22) so as to be pivotally movable about a pivot axis (23), and
   a bearing structure (27) that pivotably supports the second branch (17) including two bearing elements (28, 29) which are coaxially arranged with respect to each other and, together, form a divided bearing journal,
   wherein the bearing structure (27) is formed on a bearing insert (24) which is connected to the base (22).

2. The forceps instrument according to claim 1, wherein the bearing insert (24) has a connecting structure (32) which supports the bearing insert (24) in the base (22) in a stationary manner.

3. The forceps instrument according to claim 2, wherein the bearing insert (24) comprises two mirror-symmetrically formed bearing parts (25, 26) on which the bearing structure (27) and connecting structure (32) are formed.

4. The forceps instrument according to claim 1, wherein the bearing insert (24) is configured to be inserted in the base (22) transversely with respect to the pivot axis (23).

5. The forceps instrument according to claim 1, wherein the base (22) has a receiving compartment (39) for the bearing insert (24), wherein the base (22) has a first window (40) configured to receive the second branch (17) and a second window (41) for receiving the bearing insert (24) in the receiving compartment (39).

6. The forceps instrument according to claim 1, wherein the two bearing elements (28, 29) are journals (30, 31) which face each other and are spaced apart from one another.

7. The forceps instrument according to claim 1, wherein the second branch (17) has, on two sides which face away from each other, two coaxially arranged openings (45, 46) which act as a pivot bearing.

8. The forceps instrument according to claim 1, wherein the bearing elements (28, 29) are cylindrical.

9. The forceps instrument according to claim 1, wherein the coaxially arranged bearing elements (28, 29) comprise a rotation angle limiting device (60, 60') that limits a maximum angle of rotation of the second branch.

10. The forceps instrument according to claim 9, wherein the second branch (17) comprises—on two sides facing away from each other—two circular openings (45, 46), which are arranged coaxially with respect to each other, each of said openings having a radially inward-directed projection that is adapted to interact with the rotation angle limiting device (60, 60') to limit the maximum angle of rotation of the second branch.

11. The forceps instrument according to claim 1, wherein the bearing insert (24) is formed of a plastic material.

12. The forceps instrument according to claim 1, wherein the bearing insert (24) has guide elements (33, 34) on sides of the bearing insert facing away from each other, which, together with a complementary structure formed in the base (22), define a guiding direction (F) which is oriented transversely with respect to the pivot axis (23), wherein the guide elements (33, 34) are polygonally delimited projections.

13. The forceps instrument according to claim 12, wherein individual ones of the polygonally delimited projections have an acute-angled corner (52) which, with the forceps instrument (10) closed, points in a direction of force ($F_{LR}$) to cause a self-clamping in the one direction of force due to its geometric configuration with the forceps instrument closed.

14. The forceps instrument according to claim 1, further comprising a detent device between the bearing insert (24) and the base (22).

15. A method for assembling the forceps instrument according to claim 1, comprising:
   providing the bearing structure (27) in the form of a stretched part, in which two bearing parts (25, 26) and a connecting strip (62) are arranged in a common plane,
   moving the bearing parts (25, 26) into two parallel, spaced apart planes;
   at least one of bending, removing, or interrupting the connecting strip; and
   inserting the bearing structure (27) into the compartment (39).

* * * * *